United States Patent [19]

Fox et al.

[11] Patent Number: 4,879,213

[45] Date of Patent: Nov. 7, 1989

[54] SYNTHETIC POLYPEPTIDES AND ANTIBODIES RELATED TO EPSTEIN-BARR VIRUS EARLY ANTIGEN-DIFFUSE

[75] Inventors: Robert I. Fox, La Jolla; Richard Houghton, Solana Beach, both of Calif.

[73] Assignee: Scripps Clinic and Research Foundation, La Jolla, Calif.

[21] Appl. No.: 938,643

[22] Filed: Dec. 5, 1986

[51] Int. Cl.$^4$ ............... G01N 33/569; A61K 39/12
[52] U.S. Cl. ........................... 435/5; 424/89; 530/324; 530/325; 530/326; 530/327; 530/328; 530/329; 435/7; 435/810
[58] Field of Search ............... 435/5, 7, 810; 424/89; 530/324–329

[56] References Cited

U.S. PATENT DOCUMENTS 4,654,419  3/1987  Vaughan et al. ............... 530/327
4,707,358  11/1987  Kieff et al. ............... 530/350

OTHER PUBLICATIONS

Green et al., *Cell*, 28:477–487 (1982).
A. L. Lehninger, *Biochemistry*, pp. 57–58, Worth Publishers, Inc., 1975.
Henle et al., "Differential Reactivity of Human Serums with Early Antigens Induced by Epstein-Barr Virus", Science, 169 (1970) 188–190.
Cho et al., "Localization of the Coding Region for an Epstein-Barr Virus Early Antigens and Inducible Expression of this 60-Kilodalton Nuclear Protein in Transfected Fibroblast Cell Lines", J. Virol. 56 (1985), 852–859.
Baer et al., "DNA Sequence and Expression of the B95-8 Epstein-Barr Virus Genome", Nature, 310 (1984) 207–211.
Halprin et al., "Enzyme-Linked Immunosorbent Assay of Antibodies to Epstein-Barr Virus Nuclear and Early Antigens in Patients with Infectious Mononucleosis and Nasopharyngeal Carcinoma", Ann. Int. Med. 104 (1986) 331-7.
Pearson et al., "Identification of Polypeptide Components of the Epstein-Barr Virus Early Antigen Complex with Monoclonal Antibodies", J. Virol. 47 (1983) 193–201.
Luka et al., "A Sensitive Enzyme-Linked Immunosorbent Assay (ELISA) Against the Major EBV-Associated Antigens. I. Correlation Between ELISA and Immunofluorescence Titers Using Purified Antigens", J. Immunol. Meth., 67 (1984) 145–156.
Rhodes et al., "Human Immune Responses to Synthetic Peptides from the Epstein-Barr Nuclear Antigen", J. Immunol., 134 (1985) 211–216.
Glaser et al., "Functional Mapping of the Esptein-Barr Virus Genome: Identification of Sites Coding for the Restricted Early Antigen, the Diffuse Early Antigen, and the Nuclear Antigen", Virol. 129 (1983) 188–198.
Cho et al., "Epstein-Barr Virus (P3HR-1) Defective DNA Codes for Components of Both the Early Antigen and Viral Capsid Antigen Complexes", Virol., 137 (1984) 9–19.
Dölken et al., "Characterization of the Epstein-Barr Virus-Induced Early Polypeptide Complex p50/58 EA-D Using Rabbit Antisera, a Monoclonal Antibody, and Human Antibodies", Virol., 157 (1987) 460–471.
Wong et al., "Identification and Mapping of Epstein-Barr Virus Early Antigens and Demonstration of a Viral Gene Activator that Functions in Trans", J. Virol., 60 (1986) 149–156.

*Primary Examiner*—Christine M. Nucker
*Attorney, Agent, or Firm*—Dressler, Goldsmith, Shore, Sutker & Milnamow, Ltd.

[57] ABSTRACT

A synthetic polypeptide that contains about 6 to about 40 amino acid residues that immunologically mimics the early antigen-diffuse (EA-D) protein of the Epstein-Barr virus (EBV) is disclosed, as are receptors raised to that polypeptide, methods of their use and a reagent system. A polypeptide of the present invention has an amino acid residue sequence that corresponds to the sequence of the EBV EA-D protein from about position 350 to about position 362 from the amino-terminus.

17 Claims, 5 Drawing Sheets

SYNTHETIC POLYPEPTIDES AND ANTIBODIES RELATED TO EPSTEIN-BARR VIRUS EARLY ANTIGEN-DIFFUSE

DESCRIPTION

This invention was made with the support of the United States Government, and the United States Government has certain rights in the invention.

TECHNICAL FIELD

The present invention relates to immunogens, antigens, inocula, antibodies, methods and systems useful in the treatment and diagnosis of diseases involving Epstein Barr virus, and its early antigen-diffuse.

BACKGROUND OF THE INVENTION

The Epstein-Barr virus (EBV) is an extremely common environmental agent infecting 80-100 percent of the individuals around the world. It is the causative agent of infectious mononucleosis (IM) in humans, EBV has also been implicated in the pathogenesis of Burkitt's lymphoma (BL), nasopharyngeal carcinoma (NPC), and B lymphocyte neoplasms arising in immunosuppressed patients. Circumstantial evidence has also indicated a possible role for this virus in human autoimmune disease such as rheumatoid arthritis and Sjogren's Syndrome.

The initial or primary EBV infection may be acute or sub-clinical. Acute viral infection leads to the production of specific nuclear antigens (termed EBNA-I and EBNA-II), an "early antigen" (EA) complex, viral capsid antigens (VCA), and other virus-associated molecules. This is followed by a long period during which the EBV infection is latent in B lymphocytes present in the circulating blood, lymph nodes, spleen and salivary glands.

A latent infection is one in which a virus is present intracellularly in an unexpressed or partially expressed state. Latent viral infections can be reactivated. Although the host factors that control latency in vivo are poorly understood, there is some evidence to suggest that failure of one or more immune mechanisms is an important factor.

The serological and cell-mediated immune responses that follow primary infection by EBV are well documented and reflect the host's response to the viral immunogenic determinants expressed during the course of infection. In the context of native viral proteins, immunogenic determinants are those parts of a protein that elicit the antibody response when the whole, native protein is used as immunogen. These immunogenic determinants are believed to be confined to a few loci on the molecule.

On the other hand, a region of a protein molecule to which an antibody can bind is defined as an antigenic determinant. The detection of viral antigenic determinants in tissues as well as the profile of the patient's response to viral immunogenic determinants are becoming increasingly useful in the diagnosis of EBV-associated diseases.

The EA complex is of particular interest since antibodies to this complex are frequently present in high titers in patients with EBV-associated diseases as opposed to latently infected but non-diseased control populations. That is, humans acutely infected with Epstein-Barr virus (EBV) develop antibodies against a diffuse early antigen (EA-D). Subsequently, anti-EA-D antibodies disappear as the virus enters a phase of latency and do not reappear unless the virus is reactivated.

The EA complex is now known to consist of two distinct protein antigens designated diffuse (D) and restricted (R) based on the distribution of immunofluorescent staining in EBV-infected cells. Antibody to EA-D causes diffuse staining of the nucleus and cytoplasm in both acetone- and methanol-fixed cells. In contrast, EA-R staining is restricted to the cytoplasm in acetone-fixed cells and is not present in methanol-fixed cells.

The anti-EA activity of sera of patients with IM and NPC is directed primarily against EA-D, whereas immunoreactivity in sera of patients with BL is directed mainly against EA-R. In addition, antibodies to the EA complex are of importance in patients with EBV-associated malignancies since antibody titers tend to vary with disease course.

Thus, assays for the presence of both EA-D and anti-EA-D antibodies are of importance in several common clinical situations.

Anti-EA-D antibodies have heretofore been assayed using EA-D antigen obtained from EBV-infected cells. The immunofluorescent technique of Henle et al., *Science*, 169, 188-190 (1970) uses whole-cell preparations without any antigen purification. However, the use of such crude preparations results in false positive results for patients whose serum also contains antibodies to mammalian nuclear and cytoplasmic antigens.

More recently, Luka et al., *J. Immunol. Meth.*, 67, 145-156 (1984), reported developing an enzyme-linked immunosorbent assay (ELISA) for anti-EA-D antibodies using EA-D target antigen purified from EBV-infected cells by immunoaffinity chromatography. While the method of Luka et al. diminishes the false-positive problem associated with the use of whole cell preparations, it still requires production and handling of infectious materials.

Accordingly, it would be desirable to develop improved reagents and methods for assaying for the presence of EA-D and anti-EA-D antibodies in a body sample so as to allow diagnosis of EBV involvement in disease, as well as diagnosis of the stage of a disease such as infectious mononucleosis (IM), and limit or avoid handling of infected cell cultures.

Recent studies have shown that chemically synthesized polypeptides corresponding to short linear segments of a protein's primary amino acid residue sequence can be used to induce antibodies that immunoreact with the native protein, Lerner et al., *Nature*, 299, 592 (1982) and Sutcliffe et al., *Science*, 219, 260 (1983). In addition, some studies have shown that synthetic polypeptides can immunoreact with antibodies induced by native proteins. Rhodes et al., *J. Immunol.* 134, 211 (1985). Thus, some synthetic polypeptides can immunologically mimic the immunogenic and antigenic determinants of native proteins.

However, as is well known in the art, the application of synthetic peptide technology still suffers several shortcomings. For instance, the identification of peptides capable of mimicking antigenic determinants on a native protein requires knowing, inter alia, the amino acid residue sequence of the protein. Whereas the amino acid residue sequence can be predicted from the nucleic acid sequence of the gene coding for the protein, such a prediction can only be made if the correct reading frame of the gene is known.

The nucleic acid sequence of the EBV genome has been known since publication of the Baer et al., *Nature*, 310, 207 (1984) article. However, neither the EA-D protein gene nor its reading frame has heretofore been identified with the viral genome. Furthermore, even if a protein's amino acid residue sequence is known, methods for identifying the loci in the protein that constitute the immunogenic and antigenic determinants are experimental in nature and do not yield predictable results. There are at least two reasons for this. First, without knowing a protein's three-dimensional structure there is no reliable method for determining which linear segments of the protein are accessible to the host's immune system. Second, whether the three-dimensional structure is known or not, short linear polypeptides often appear not to have the ability to mimic the required secondary and tertiary conformational structures to constitute appropriate immunogenic and antigenic determinants, Tainer et al., *Nature*, 312, 127 (1984).

BRIEF SUMMARY OF THE INVENTION

One aspect this invention contemplates a synthetic polypeptide that consists essentially of about 6 to about 40 amino acid residues, and more preferably about 10 to about 25 residues, having an amino acid residue sequence corresponding to an amino acid residue sequence of the EBV EA-D protein from about position 350 to about position 362 from the amino terminus thereof. The synthetic polypeptide has the capacity to immunologically bind antibodies induced by EA-D.

A particularly preferred polypeptide has the sequence, from left to right and in the direction from amino-terminus to carboxy-terminus, represented by the formula:

H-PARPETPSAAIPS-OH.

Another aspect of the present invention contemplates a synthetic polypeptide oligomer of about 12 to about 40 amino acid residues and containing a plurality of joined synthetic polypeptide repeating units wherein at least two of the units are synthetic polypeptides as described before.

Still another aspect of the present invention contemplates a synthetic polypeptide polymer containing a plurality of synthetic polypeptide repeating units joined together by other than polypeptide bonds, and containing more than about 100 amino acid residues. The repeating units are synthetic polypeptides as described before.

Yet another aspect of this invention contemplates is a method for assaying a body fluid sample for the presence of antibodies to EA-D comprising the steps of providing a body fluid sample to be assayed and a synthetic polypeptide as described before. The body fluid sample and polypeptide are admixed to form an immunoreaction admixture. The admixture is maintained under biological assay conditions for a predetermined time period sufficient for any anti-EA-D antibodies present in the sample to immunologically bind the polypeptide to form an immunoreactant. The presence of any immunoreactant that formed in the admixture is then determined.

A further aspect of this invention contemplates a method for assaying a body sample for the presence of EA-D comprising the steps of providing a body sample to be assayed and biologically active receptor molecules that contain an antibody combining site induced by a synthetic polypeptide as described before. The body sample is admixed with the receptors to form an immunoreaction admixture. The admixture is maintained under biological assay conditions for a predetermined time period sufficient for any EA-D present in the sample to be immunologically bound by the receptors to form an immunoreactant. The presence of any immunoreactant formed in the admixture is then determined.

A still further aspect of the present invention contemplates a diagnostic system for assaying for the presence of anti-EA-D antibodies in a body fluid sample. The system comprises, preferably in separate containers, a synthetic polypeptide as described before and a labeled specific binding agent for signaling the immunoreaction of the polypeptide with anti-EA-D antibodies.

Further contemplated is an inoculum constituted by a synthetic polypeptide as described before linked to a carrier and dispersed in a physiologically tolerable diluent.

Also contemplated is a receptor raised to a synthetic polypeptide as described before, the receptor being capable of immunoreacting with the EA-D protein.

In another aspect, the present invention contemplates a method for assaying for the presence of EA-D in a body sample, preferably lysed peripheral blood lymphocytes. The body sample is admixed with the above described receptors to form an immunoreaction admixture. The admixture is maintained under biological assay conditions for a predetermined time period sufficient for any EA-D present in the sample to immunoreact with the receptors to form an immunoreactant. The presence of any immunoreactant formed in the admixture is then determined.

Another aspect of the present invention is a diagnostic system for assaying for the presence of EA-D in a body sample. The system comprises, preferably in separate packages, receptors as described before and a labeled specific binding agent for signaling the immunoreaction of the receptors with EA-D protein.

One advantage provided by the present invention is the ability to produce antigens and receptors related to EBV EA-D without handling infectious material.

The present invention is also advantageous because it provides antigens and receptors having high immunologic specificity that are substantially free from false positive results caused by naturally occurring nuclear and cytoplasmic antigens.

Another advantage of the present invention is that it provides for early detection of a reactivated latent EBV infection.

Still further advantages of the present invention will be apparent to those skilled in the art from the description that follows.

BRIEF DESCRIPTION OF THE DRAWINGS

In the Figures forming a portion of the disclosure of this invention:

FIG. 1 illustrates the complete amino acid residue sequence of the EA-D protein, from left to right and in the direction of amino-terminus to carboxy-terminus, as translated from the EA-D gene nucleic acid sequence [EBV genome nucleic acid residues 79899–81110) published by Baer et al., *Nature*, 310, 207 (1984)], and using single-letter amino acid residue abbreviations. The locations of the amino acid residue sequences of the polypeptides used in the present study are indicated by dashed lines under the sequence, with terminal residues being indicated by "+" signs directly under the terminal residues. The dashed lines are interrupted by the designations K5, K6, K7, K8 and K9, which designations are utilized herein for reference to those polypeptides.

The data of Panel A show that the frequency of IgM antibody immunological binding (immunoreactant formation) to EA-D epitopes mimicked by polypeptide K7 is greater in acute IM patients than in normal individuals. The data of Panels B and C show similar results for IgG and IgA antibody responses, respectively.

Figure 3:
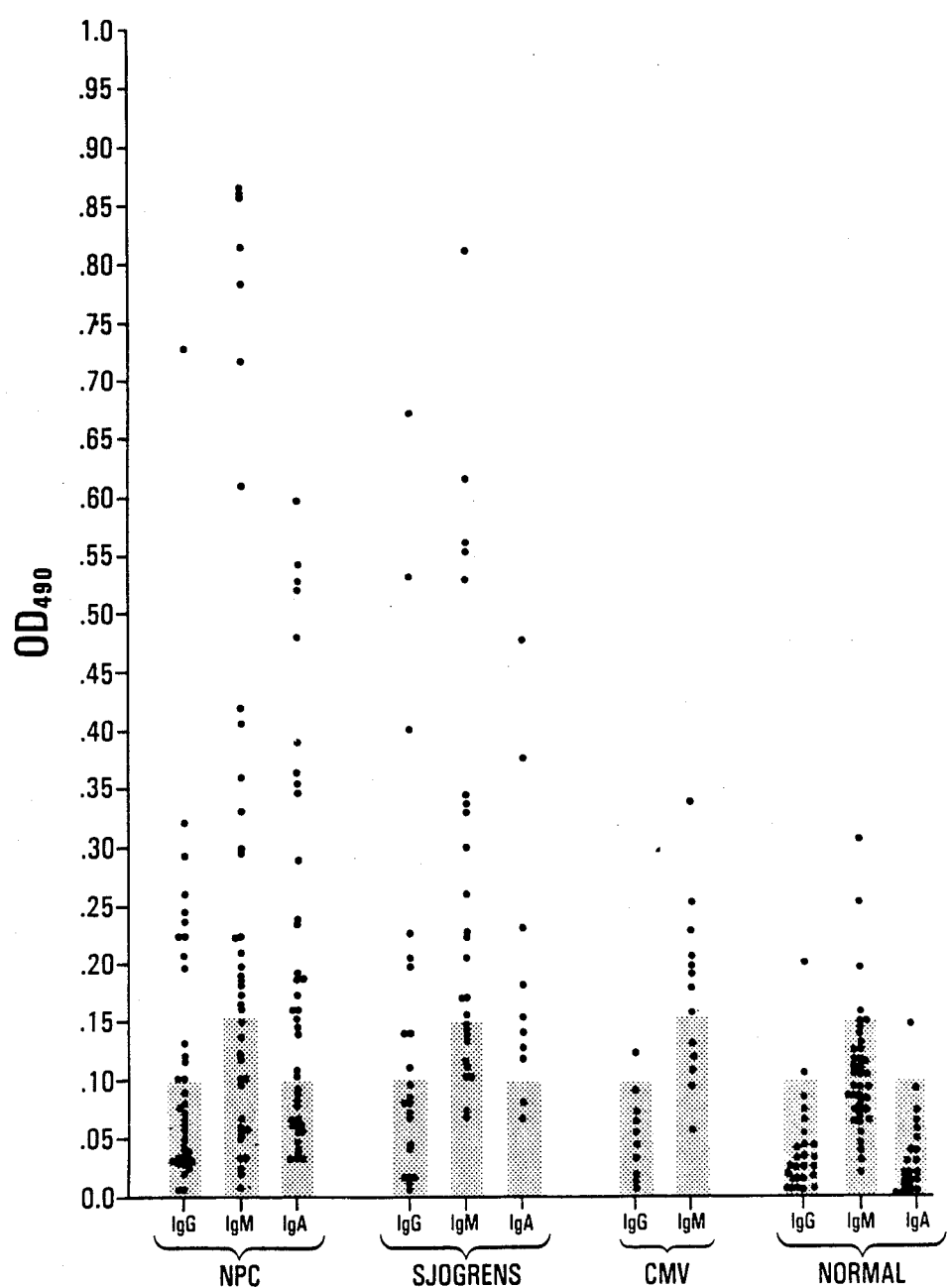

FIG. 3 is a histogram illustrating the results obtained from using the polypeptide K7 ELISA of Example 5 to assay sera from patients having nasopharyngeal carcinoma (NPC), Sjogren's Syndrome (SS), cytomegalovirus (CMV) infection and normal donors. The amount of anti-EA-D antibody in each serum sample that immunoreacted with polypeptide K7 is expressed as an OD 490 value and is indicated by a dot on the histogram.

Figure 4:
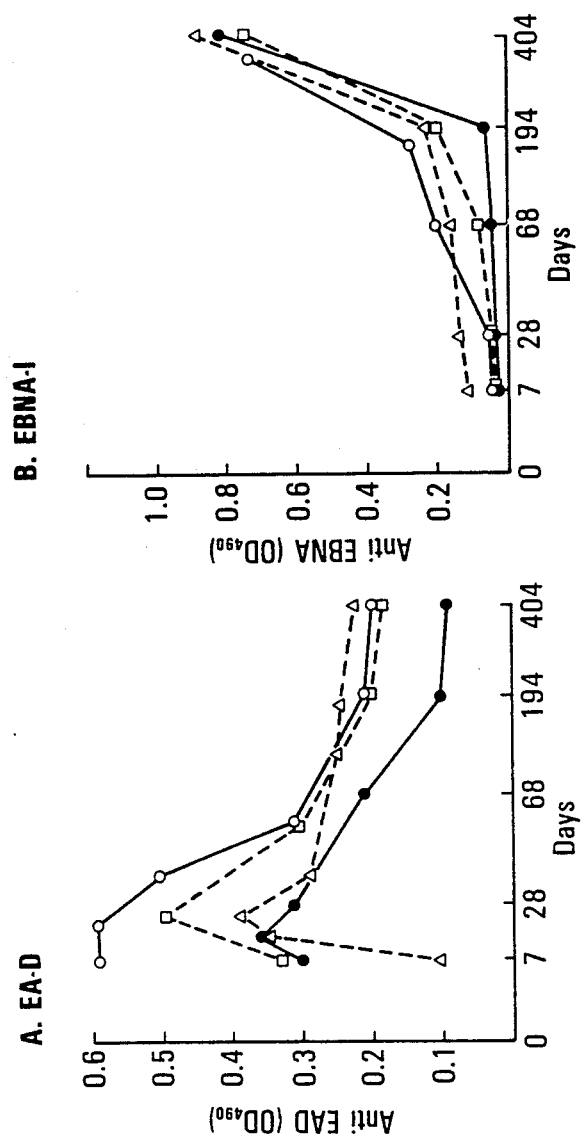

FIG. 4 contains two graph panels that illustrate the results of assaying serial serum samples from 4 patients with acute IM for anti-EA-D antibodies using the anti-EA-D antibody ELISA with polypeptide K7 as solid phase target as described in Example 5. Data from each patient's sera are represented by a different symbol, with the same symbol being used for the same patient in each graph panel. The data of Panel A illustrate that anti-EA-D IgM antibodies can be detected in IM patients one week after onset of symptoms. The data of Panel B illustrate confirmation of IM diagnosis in the same paitents by detecting the increase of anti-EBNA-1 antibodies in the serum samples using the anti-EBNA-1 ELISA described in Rhodes et al., *J. Immunol.*, 134, 211 (1985).

Figure 5:
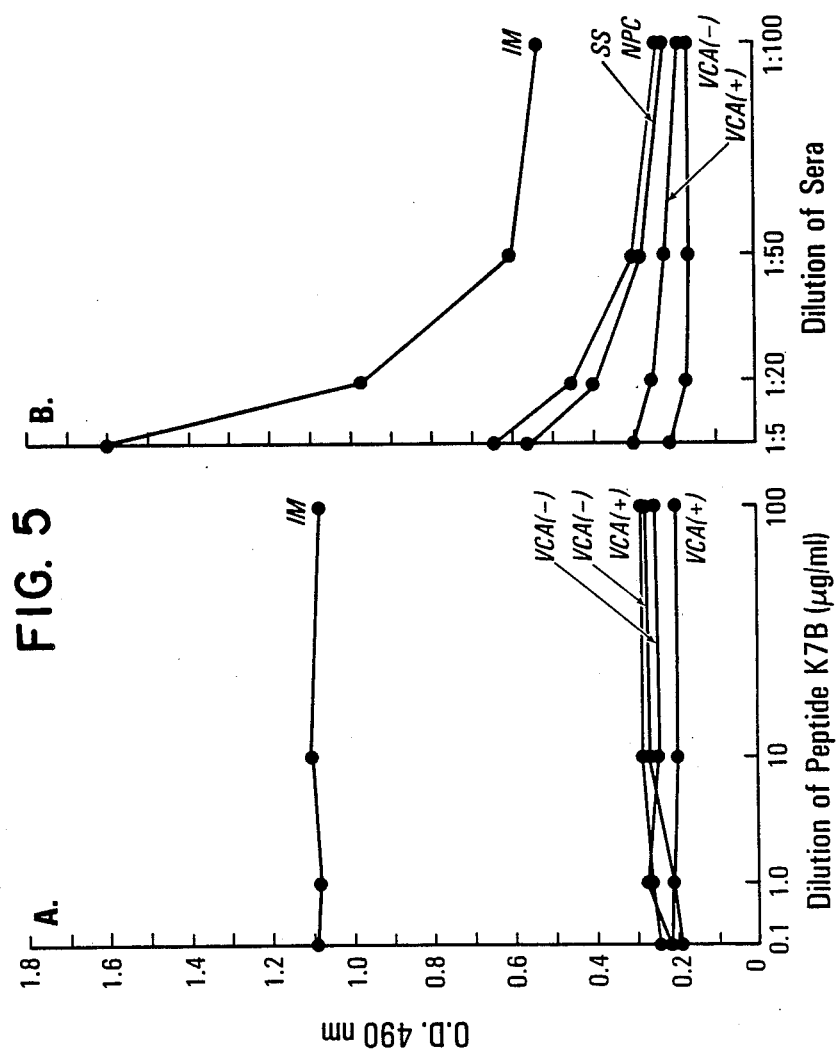

FIG. 5 contains two graph panels that show the effect of serum dilution and polypeptide concentration on results obtained with the anti-EA-D IgM antibody ELISA using K7 as solid phase target.

The data of Panel A illustrate the effect varying the amount of K7 polypeptide affixed to the microtiter plate wells has on the ability of the anti-EA-D antibody ELISA to assay anti-EA-D IgM antibodies in serum sample from IM patients (IM) and normal individuals whose sera were free from antibodies to EBV capsid protein antigens (VCA−) and patients whose sera contained antibodies to those antigens (VCA−), respectively. The microtiter plate wells were coated with polypeptide K7 as described in Example 5, except that concentrations of the polypeptide K7-containing solution used to affix K7 to the well walls varied as shown in micrograms per milliliter (ug/ml). The sera tested were all diluted 1:20 before use.

The data of Panel B illustrate the effect of serum dilution on detection of human IgM antibodies that immunoreact with synthetic polypeptide K7. Microtiter plate well walls were coated with K7 using a 10 ug/ml solution as described in Example 5. Sera from patients with IM, NPC and SS as well as from VCA− and VCA+ normal individuals were then assayed in the anti-EA-D ELISA at the dilutions shown.

DETAILED DESCRIPTION OF THE INVENTION

A. Definitions

The term "antibody" refers to a molecule that is a member of a family of glycosylated proteins called immunoglobulins, that can specifically combine with an antigen.

An "antibody combining site" is that structural portion of an antibody molecule comprised of heavy and light chain variable regions that specifically binds antigen.

The word "antigen" has been used historically to designate an entity that is bound by an antibody, and also to designate the entity that induces the production of the antibody. More current usage limits the meaning of antigen to that entity bound by an antibody, whereas the word "immunogen" is used for the entity that induces antibody production. Where an entity discussed herein is both immunogenic and antigenic, it will generally be termed an antigen.

"Antigenic determinant" refers to the actual structural portion of the antigen that is immunologically bound by an antibody combining site. The term is also used interchangeably with "epitope".

The term "antigenically related variants" is used herein to designate polypeptides of differing overall amino acid residue sequence that share at least a portion of one antigenic determinant and are therefore immunologically crossreactive. That is, the polypeptide sequences of antigenically related variants are different, but antibodies raised to each variant immunoreact with the other.

The term "biologically active" refers at least to the ability of a receptor to at least specifically bind an appropriate ligand although other general or effector capability can also be present.

The word "complex" as used herein refers to the product formed when a specific binding agent binds to a target ligand. Exemplary complexes are immunoreactants, protein A bound to an antibody and the like.

The term "conservative substitution" as used herein denotes that one amino acid residue has been replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that antibodies raised to such a polypeptide also immunoreact with the corresponding polypeptide having the unsubstituted amino acid.

The term "corresponds" in its various grammatical forms as used in relation to peptide sequences means the peptide sequence described plus or minus up to three amino acid residues at either or both of the amino- and carboxytermini and containing only conservative substitutions in particular amino acid residues along the polypeptide sequence.

"ELISA" refers to an enzyme-linked immunosorbent assay that employs an antibody or antigen bound to a solid phase and an enzyme-antigen or enzyme-antibody conjugate to detect and quantify the amount of antigen or antibody present in a sample. A description of the ELISA technique is found in Chapter 22 of the 4th Edition of *Basic and Clinical Immunology* by D.P. Sites et al., published by Lange Medical Publications of Los Altos, CA in 1982 and in U.S. Pat. Nos. 3,654,090; 3,850,752; and 4,016,043, which are all incorporated herein by reference.

"Enzyme" refers to a protein capable of accelerating or producing by catalytic action some change in a substrate for which it is often specific.

"Epitope" refers to that portion of a molecule that is specifically bound by an antibody combining site to form an immunoreactant. It also is referred to as the determinant or antigenic determinant.

The phrase "immunologically mimics" is used herein to mean that a polypeptide of this invention can: (1) be immunologically bound by antibodies induced by native protein; and (2) induce production of antibodies that bind to the inducing polypeptide and also to the native protein.

The term "immunoreact" in its various forms means binding between an antigen as a ligand and a molecule containing an antibody combining site such as a portion of or a whole antibody as the receptor.

"Immunoreactant" as used herein refers to the product of an immunological reaction; i.e., that entity produced when a ligand is immunologically bound by a receptor molecule.

The terms "labeling means", "indicating group" or "label" are used interchangeably herein to include single atoms and molecules that are either directly or indirectly involved in the production of a detectable signal to indicate the presence of a immunoreactant. Any labeling means can be linked to or incorporated in a receptor or used separately, and those atoms or molecules can be used alone or in conjunction with additional reagents. Such indicating groups or labels are themselves well-known in immunochemistry and constitute a part of this invention only insofar as they are utilized with otherwise novel receptors, methods and/or systems.

"Ligand" refers to a molecule that contains a structural portion that is bound by a specific receptor.

The words "peptide" and "polypeptide" are used interchangeably herein for a known sequence of amino acid residues linked together by peptide bonds.

The phrase "pharmaceutically acceptable salts", as used herein, refers to non-toxic alkali metal, alkaline earth metal and ammonium salts used in the pharmaceutical industry, including the sodium, potassium, lithium, calcium, magnesium and ammonium salts and the like that are prepared by methods well-known in the art. The phrase also includes non-toxic acid addition salts that are generally prepared by reacting the compounds of this invention with a suitable organic or inorganic acid. Representative salts include the hydrochloride, hydrobromide, sulfate, bisulfate, acetate, oxalate, valerate, oleate, laurate, vorate, benzoate, lactate, phosphate, tosylate, citrate, maleate, fumarate, succinate, tartrate, and the like.

The term "receptor" is used herein to indicate a biologically active molecule comprised of an antibody combining site that immunologically binds to (or with) an antigen. Such binding typically occurs with an affinity of about $10^5$ to about $10^{10}$ liters per mole and is a specific interaction of the epitope of the antigen with the antibody combining site of the receptor.

Biological activity of a receptor molecule is evidenced by the immunologic reaction of the receptor with its antigenic ligand upon their admixture in an aqueous medium to form an immunoreactant, at least at physiological pH values and ionic strengths. Preferably, biological activity occurs under biological assay conditions; i.e., those wherein the receptors of this invention bind to the antigenic ligand within a pH value range of about 5 to about 9, and at ionic strengths such as that of distilled water to that of about one molar sodium chloride.

Receptors are comprised of an antibody combining site capable of binding specifically to antigen. Receptors include the Fab, FAB', F(ab')$_2$ and F(v) polypeptide portions of antibodies a well as antibodies and substantially whole antibodies. Fab and F(ab')$_2$ portions of antibodies are well known in the art, and are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')2 portions followed by reduction of the disulfide bonds linking the two heavy chain portions as with mercaptoethanol, and then alkylation of the resulting protein mercaptan with reagent such as iodoacetamide. Intact, whole antibodies are preferred, and will be utilized as illustrative of the monoclonal or other receptor molecules of this invention.

The words "secrete" and "produce" are often used interchangeably in the art as to cells from which antibody molecules are obtained. Cells that produce antibodies may, however, not secrete those molecules into their environment. The hybridoma cells of interest herein secrete monoclonal antibodies into their environment. Nevertheless, such cells are often referred to herein as "antibody-producing" cells, and their antibodies are referred to as being "produced" in keeping with the phrase utilized in the art.

The term "synthetic" as used herein means that the polypeptide molecule or polypeptide repeating unit has been built up by chemical means; i.e., chemically synthesized, rather than being prepared by a biological means; as by genetic engineering techniques. Thus, the synthetic polypeptides embodying the present invention are free from naturally occurring proteins and fragments thereof.

B. Synthetic Polypeptides

Figure 1:
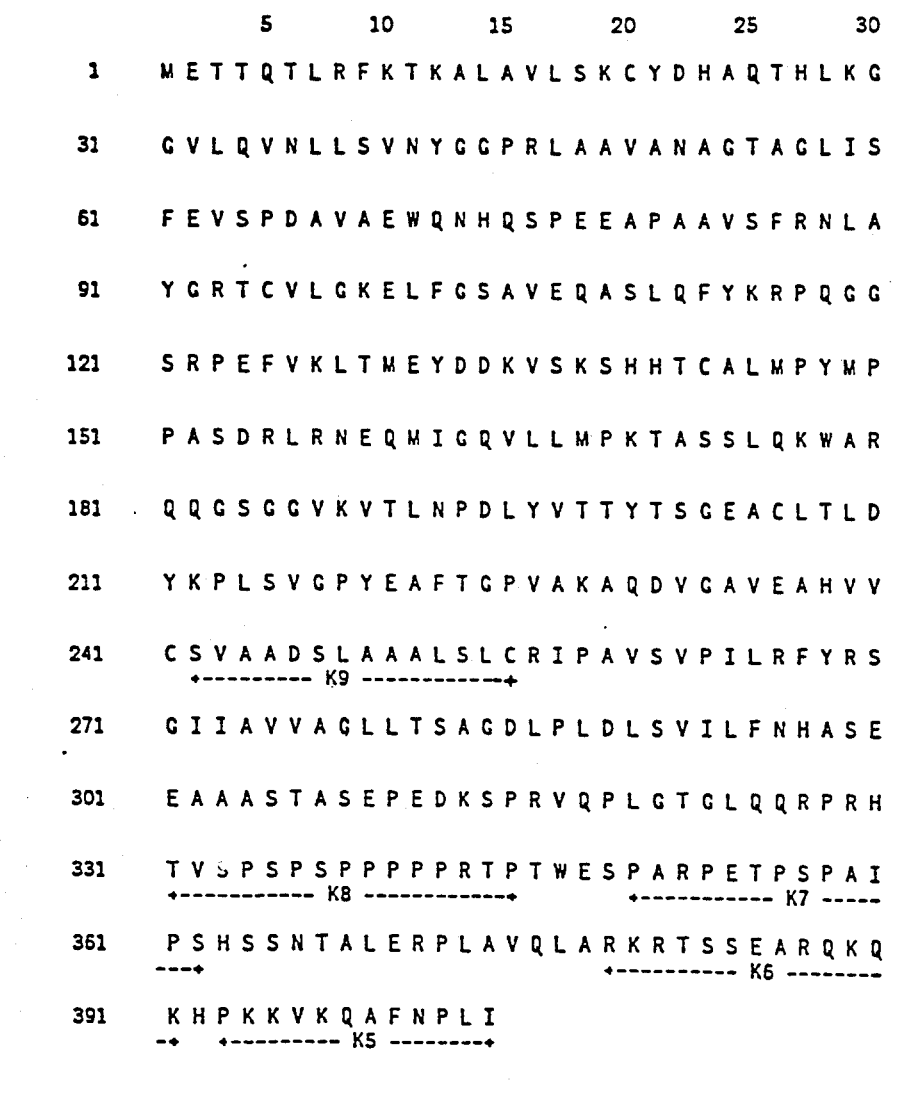

A synthetic polypeptide of the present invention consists essentially of about 6 to about 40 amino acid residues, and more preferably about 10 to about 24 residues, having an amino acid residue sequence corresponding to an amino acid residue sequence of the EBV EA-D protein from about position 350 to about position 362 from the amino terminus thereof, using the positions assigned in FIG. 1 and the genomic sequence of Baer et al., *Nature*, 310, 207 (1984). The synthetic polypeptide has the capacity to immunologically bind antibodies induced by EA-D.

In preferred practice, the polypeptide when linked to an immunogenic carrier such as keyhole limpet hemocyanin (KLH) as a conjugate and introduced in an effective amount in an aqueous diluent into a host mammal such as a rat, mouse, rabbit or guinea pig, is capable of inducing secretion of antibodies that not only immunoreact with the polypeptide of the conjugate, but also immunoreact with EA-D in the denatured state. More preferably, those induced antibodies further immunoreact with EA-D in the native state. Thus, in preferred embodiments, a polypeptide of the present invention can immunologically mimic immunogenic and antigenic determinants of the native EA-D protein.

Exemplary of EA-D in the native state is the protein as it is found in body fluids such as blood plasma of patients with acute IM. Exemplary of EA-D in the denatured state is that protein after reduction with 2-mercaptoethanol as is used in SDS-PAGE and Western blotting analyses.

Preferred amino acid residue sequences include the sequence, taken from left to right and in the direction of amino-terminus to carboxy-terminus, represented by the formula:

-PARPETPSPAIPS-;

pharmaceutically acceptable salts thereof, and antigenically related variants thereof.

It is noted that a dash at the beginning or end of an amino acid residue sequence indicates a bond to a radical such as H and OH, at the amino- and carboxy-termini, respectively, or a further sequence of one or more amino acid residues up to a total of forty amino acid residues in the polypeptide chain.

It is further noted that the sequence of the amino acid residues that can be present in the polypeptide in addition to the at least six amino acid residue sequence that corresponds to an amino acid residue sequence of the EA-D protein from about position 350 to about position 362 from the amino-terminus can be irrelevant so long as the essential character of the polypeptide in immunologically binding to antibodies induced by EA-D is not impaired substantially. More preferably, the characteristic immunogenicity in inducing antibodies that immunoreact with the polypeptide and at least denatured EA-D as discussed before is also not substantially impaired.

Most preferably, the polypeptide consists essentially of one or more amino acid residue sequences that are identical to the before-discussed positions of the EA-D protein molecule. Those most preferred polypeptides that contain a plurality of amino acid residue sequences that are identical to a sequence of EA-D as described before are within a group of compounds referred to herein as "polypeptide oligomers", and are discussed hereinafter.

A particularly preferred polypeptide has an amino acid residue sequence corresponding to the sequence, taken from left to right and in the direction from amino-terminus to carboxy-terminus, represented by the formula:

H-PARPETPSPAIPS-OH;

pharmaceutically acceptable salts thereof and antigenically related variants thereof.

As can be seen by reference to FIG. 1, the above polypeptide has an amino acid residue sequence that is identical to that of positions 350 through 362 of EA-D, based upon the Baer et al. genomic sequence.

A polypeptide of the present invention can be synthesized by any techniques that are known to those skilled in the polypeptide art. An excellent summary of the many techniques so available may be found in J.M. Steward and J.D. Young, "Solid Phase Peptide Synthesis", W.H. Freeman Co., San Francisco, 1969; J. Meienhofer, "Hormonal Proteins and Peptides", Vol. 2, p. 46, Academic Press (New York), 1973 for solid phase peptide synthesis; and E. Schroder and K. Kubke, "The Peptides", Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

All amino acid residues identified herein are in the natural of L-configuration. In keeping with standard polypeptide nomenclature, [J. Biol. Chem., 243, 3557–59 (1969)], abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L—tyrosine |
| G | Gly | L—glycine |
| F | Phe | L—phenylalanine |
| M | Met | L—methionine |
| A | Ala | L—alanine |
| S | Ser | L—serine |
| I | Ile | L—isoleucine |
| L | Leu | L—leucine |
| T | Thr | L—threonine |
| V | Val | L—valine |
| P | Pro | L—proline |
| K | Lys | L—lysine |
| H | His | L—histidine |
| Q | Gln | L—glutamine |
| E | Glu | L—glutamic acid |
| Z | Glx | L—glutamic acid or L—glutamine |
| W | Trp | L—tryptophan |
| R | Arg | L—arginine |
| D | Asp | L—aspartic acid |
| N | Asn | L—asparagine |
| B | Asx | L—aspartic acid or |

-continued

| TABLE OF CORRESPONDENCE SYMBOL | | |
| --- | --- | --- |
| 1-Letter | 3-Letter | AMINO ACID |
| | | L—asparagine |
| C | Cys | L—cysteine |

C. Polypeptide Oligomers

The present invention also contemplates a synthetic polypeptide oligomer containing a plurality of joined synthetic polypeptide repeating units wherein at least two of the repeating units are polypeptides of this invention, as were previously discussed. Such an oligomer contains a total of about 12 to about 40 amino acid residues, and more preferably about 25 to about 40 residues. The individual repeating units can be about 6 to about 34 residues in length where two polypeptide repeating units are present. As noted before, more preferably, all of the repeating units are not only polypeptides of this invention, but are polypeptides whose amino acid residue sequences are identical to the sequence of EA-D.

A polypeptide oligomer of this invention is also characterized by having the capacity to immunologically bind to antibodies induced by EA-D. More preferably, a polypeptide oligomer is further characterized by having the capacity when linked to an immunogenic carrier such as KLH and introduced in an aqueous diluent composition into a host mammal as described before of inducing secretion of antibodies that immunologically bind to EA-D.

A particularly preferred polypeptide oligomer contains a plurality of the particularly preferred synthetic polypeptides of this invention having the amino acid residue sequence, from left to right and in the direction from aminoterminus to carboxy-terminus, represented by the formula:

-PARPETPSPAIPS-.

Using the three-letter abbreviations of the Table of Correspondence, the above polypeptide can also be represented by the formula:

-ProAlaArgProGluThrProSerProAlaIleProSer-.

Thus, the oligomeric polypeptides of this invention, like their constituent polypeptides, are antigenic to human anti-EA-D antibodies, and are more preferably immunogenic as discussed before. Those oligomeric polypeptides can therefore be used to induce the production of anti-EA-D antibodies that are useful in the diagnostic methods and systems discussed hereinafter, and can also be used as an antigen in appropriate diagnostic methods and systems.

Oligomers that contain fewer than about 35 amino acid residues in the total oligomeric polypeptide are typically linked to an immunogenic carrier such as KLH for use as an immunogen. Those oligomeric polypeptides that contain more than a total of about 35 amino acid residues are typically sufficiently immunogenic to be used without a carrier.

An oligomeric polypeptide can be prepared by bonding together the synthesized polypeptide monomers in a head-to-tail manner using the aforementioned solid phase method; i.e., one complete polypeptide sequence can be synthesized on the resin, followed one or more of the same or different polypeptide sequences, with the entire oligomeric unit thereafter being cleaved from the resin and used as described herein. Such head-to-tail polypeptide multimers preferably contain about 2 to about 5 polypeptide repeating units.

Alternatively, polypeptide oligomers can be prepared as a polymer of synthetic polypeptides used as monomers; i.e., repeating units as is described in detail herein below. Exemplary chain terminating agent for such a purpose are 2-mercaptoethanol, thioglycolic acid and thiopropionic acid.

D. Polypeptide Polymers

As used herein, the term "polypeptide polymer" in its various grammatical forms is defined as a molecule that contains a plurality of synthetic polypeptides of this invention as repeating units. Those polypeptide repeating units are joined together by other than polypeptide bonds, and the polymer includes more than about 100 amino acid residues. Thus, a polymer of this invention has an apparent molecular mass, $M_r$, of about 10,000 or more so long as it is dispersible in an aqueous composition at a pH value of about 5 to about 9, and preferably at about pH 6.5 to about 7.5. The polypeptide repeating units can be the same or different and can include one or more additional sequences other than an amino acid residue sequence of the present invention so long as any additional polypeptide present in the polymer does not substantially interfere or otherwise inhibit the immunoreaction of antibodies induced by EA-D with the polymer; i.e., interfere with the antigenicity of the polymer. The presence of a polypeptide in the polymer other than that of the invention also preferably does not substantially inhibit the immunogenicity of the polymer.

Polypeptide polymers (synthetic multimers) typically have the advantage of increased immunogenicity and antigenicity. In addition, a carrier is typically not needed when a polymeric immunogen is utilized. Where different polypeptide monomers are used to make up the polymer, the ability to immunoreact with antibodies to several EA-D antigenic determinants is obtained. A still further advantage is the ability of such a polymer when used in an inoculum to induce antibodies that immunoreact with several antigenic determinants of EA-D.

An exemplary polymer of this invention can be synthesized using the polypeptide monomers of this invention that contain added cysteine residues at both the amino- and carboxy-termini (diCys polypeptide). The diCys polypeptide monomers can be bonded together by intramolecular, interpolypeptide cysteine disulfide bonds utilizing an oxidation procedure to form an immunogenic, antigenic polymer. The polypeptide polymer so prepared contains a plurality of the synthetic polypeptides of this invention as repeating units. Those repeating units are bonded together by the above-discussed oxidized cysteine (cystine) residues.

The presence of one or two terminal Cys residues in a polypeptide of this invention for the purposes of binding the polypeptide to a carrier or for preparing a polypeptide polymer is not to be construed as altering the amino acid residue sequence of a polypeptide of this invention.

A particularly preferred polypeptide polymer contains a plurality of the particularly preferred synthetic polypeptides of this invention having the amino acid residue sequence, from left to right and in the direction from amino terminus to carboxy-terminus, represented by the formula:

-PARPETPSPAIPS-.

Thus, the synthetic multimeric polypeptides of this invention, like their constituent polypeptides, are antigenic to human anti-EA-D antibodies, and are more preferably immunogenic as discussed before. Those synthetic multimeric polypeptides can therefore be used to induce the production of anti-EA-D antibodies that are useful in the diagnostic methods and systems discussed hereinafter, and can also be used as an antigen in appropriate diagnostic methods and systems.

E. Inocula

In another embodiment, a polypeptide of this invention is used in a pharmaceutically acceptable aqueous diluent composition to form an inoculum that, when administered in an effective amount, is capable of inducing antibodies that immunoreact with EA-D.

The word "inoculum" in its various grammatical forms is used herein to describe a composition containing a polypeptide of this invention as an active ingredient used for the preparation of antibodies against EA-D. When a polypeptide is used to induce antibodies it is to be understood that the polypeptide can be used, linked to an immunogenic carrier, as an oligomeric polypeptide free or linked to a carrier as a conjugate, or as a polypeptide polymer, but for ease of expression the various embodiments of the polypeptides of this invention are collectively referred to herein by the term "polypeptide", and its various grammatical forms.

For polypeptides that contain fewer than about 35 amino acid residues, it is preferable to use an immunogenic carrier for the purpose of inducing the production of antibodies as already noted.

As also already noted, one or more additional amino acid residues can be added to the amino- or carboxy-termini of the synthetic polypeptide to assist in binding the polypeptide to a carrier. Cysteine residues added at the amino- or carboxy-termini of the synthetic polypeptide have been found to be particularly useful for forming polymers via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.*, 147, 318326 (1983) and the like, or the use of carbodiimide technology as in the use of a water-soluble carbodiimide to form amide links to the immunogenic carrier, as discussed before for linking a plurality of polypeptides together to form a synthetic multimer.

Useful immunogenic carriers are well known in the art, and are generally proteins themselves. Exemplary of such carriers are keyhole hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

As is also well known in the art, it is often beneficial to bind a synthetic polypeptide to its carrier by means of an intermediate, linking group. As noted before, glutaraldehyde is one such linking group. However, when cysteine is used the intermediate linking group is preferably an m-maleimidobenxoyl-N-hydroxysuccinimde (MBS), as was used herein.

Additionally, MBS can be first added to the carrier by an ester-amide interchange reaction as disclosed by Liu et al. *Biochem.*, 80, 690 (1979). Thereafter, the addition can be followed by addition of a blocked mercapto group such as thiolacetic acid ($CH_3COSH$) across the maleimido-double bond. After cleavage of the acyl blocking group, a disulfide bond is formed between the deblocked linking group mercaptan and the mercaptan of the added cysteine residue of the synthetic polypeptide.

The choice of carrier is more dependent upon the ultimate use of the immunogen than upon the determinant portion of the immunogen, and is based upon criteria not particularly involved in the present invention. For example, a carrier that does not generate an untoward reaction in the particular non-human host (recipient) animal should be selected.

The present inoculum contains an effective, immunogenic amount of a polypeptide of this invention, as an oligomeric polypeptide or as a polypeptide polymer of individual polypeptides linked together through oxidized, polypeptide terminal cysteine residues or as a conjugate linked to a carrier. The effective amount of polypeptide per unit dose depends, among other things, on the species of animal inoculated, the body weight of the animal and the chosen inoculation regimen as is well known in the art. Inocula typically contain polypeptide concentrations of about 10 micrograms to about 500 milligrams per inoculation (dose). The stated amounts of polypeptide refer to the weight of polypeptide without the weight of a carrier, when a carrier is used. Specific, exemplary inocula are described hereinafter with weight of carrier plus polypeptide (conjugate) being given.

The term "unit dose" refers to physically discrete units suitable as unitary dosages for animals, each unit containing a predetermined quantity of active material calculated to produce the desired therapeutic effect in association with the required diluent; i.e., carrier, or vehicle. The specifications for the novel unit dose of this invention are dictated by and are directly dependent on (a) the unique characteristics of the active material and the particular immunologic effect to be achieved, and (b) the limitations inherent in the art of compounding such active material for immunologic use in animals, as disclosed in detail in the specification, these being features of the present invention.

Inocula are typically prepared from the dried solid polypeptide-conjugate, oligomeric polypeptide or polypeptide polymer by dispersing the polypeptide-conjugate or polypeptide polymer in a physiologically tolerable (acceptable) diluent such as water, saline, phosphate-buffered saline and the like as are well known to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

F. Receptors

Antibodies and substantially whole antibodies induced by (raised to) the polypeptides of this invention as well as antibody combining sites prepared from such antibodies constitute still another embodiment of this invention. These molecules are collectively referred to herein as receptors. Receptors are raised in mammalian hosts such as mice, rabbits, goats, guinea pigs, horses and the like by immunization using the inocula described hereinabove.

Suitable receptors in monoclonal form, typically whole antibodies, can also be prepared using hybridoma technology described by Niman et al., *Proc. Natl. Sci., U.S.A.*, 80, 4949–4953 (1983), which description is incorporated herein by reference. Briefly, to form the hybridoma from which the monoclonal receptor is produced, a myeloma or other self-perpetuating cell line is fused with lymphocytes obtained from the spleen of a mammal hyperimmunized with a polypeptide of this invention.

It is preferred that the myeloma cell line be from the same species as the lymphocytes. Typically, a mouse of the strain 129 G1X′ is the preferred mammal. Suitable mouse myelomas for use in the present invention include the hypoxanthineaminopterin-thymidine-sensitive (HAT) cell lines P3X63-Ag8.653, and Sp2/0-Ag14 that are available from the American Type Culture Collection, Rockville, MD, under the designations CRL 1580 and CRL 1581, respectively.

Splenocytes are typically fused with myeloma cells using polyethylene glycol (PEG) 1500. Fused hybrids are selected by their sensitivity to HAT. Hybridomas secreting receptor molecules of this invention are identified using an enzyme-linked immunosorbent assay (ELISA) as described herein.

Monoclonal antibodies as receptors need not only be obtained from hybridoma supernatants, but can also be obtained in generally more concentrated form from ascites fluid of mammals into which the desired hybridoma has been introduced. Preparation of monoclonal antibodies using ascites fluid is well known and will not be dealt with further herein.

A receptor of this invention binds both to the polypeptide to which it was raised and also binds to the corresponding EA-D antigenic determinant site that the polypeptide of this invention immunologically mimics. Thus, a polypeptide of this invention can be both an immunogen and an antigen.

The receptors of this invention induced by a polypeptide of this invention, including an oligomeric polypeptide and a polypeptide polymer, can be described as being oligoclonal as compared to naturally occurring polyclonal antibodies since they are raised to an immunogen (the relatively small polypeptide) having relatively few epitopes as compared to the epitopes mimicked by an intact EA-D molecule. Consequently, receptors of this invention bind to epitopes of the polypeptide, whereas naturally occurring antibodies raised to the whole EA-D molecule bind to epitopes throughout the EA-D molecule and are referred to as being polyclonal.

F. Assay Methods and Systems

1. Assays for Anti-EA-D Antibodies

The synthetic polypeptide of the present invention is particularly useful for assaying for the presence and amount of anti-EA-D antibodies in a liquid body sample such as blood, serum or plasma.

In one embodiment, the present invention contemplates a method for assaying a body sample for the presence of anti-EA-D antibodies comprising the steps of:

(a) Providing a body fluid sample to be assayed. Typically such sample is provided as a known amount of blood and more preferably as serum or plasma. Methods for providing samples of blood, plasma and serum are well known in the art and will not be discussed further herein.

(b) Providing a synthetic polypeptide consisting essentially of about 6 to about 40 amino acid residues having an amino acid residue sequence substantially corresponding to an amino acid residue sequence of the EA-D protein from about position 350 to about position 362 from the amino-terminus thereof, the synthetic polypeptide having the capacity to be immunologically bound by antibodies induced by EA-D.

(c) Admixing the body fluid sample with the polypeptide to form an immunoreaction admixture.

(d) Maintaining the admixture under biological assay conditions for a predetermined time period such as about 10 minutes to about 16–20 hours at a temperature of about 4 degrees C to about 45 degrees C that is sufficient for any anti-EA-D antibodies present in the sample to immunologically bind the polypeptide to form a first immunoreactant.

Biological assay conditions are those that maintain the biological activity of the polypeptide molecules of this invention and the anti-EA-D antibodies sought to be assayed, and include a temperature range of about 4 degrees C to about 45 degrees C, a pH value range of about 5 to about 9 and an ionic strength varying from that of distilled water to that of about one molar sodium chloride. Methods for optimizing such conditions are well known in the art.

(e) Assaying for the presence of any immunoreactant that formed, and thereby the presence of any anti-EA-D antibodies in the immunoreaction admixture.

Assaying for the presence of anti-EA-D antibody containing immunoreactant, either directly or indirectly, can be accomplished by assay techniques well known in the art. For example, a homogeneous assay system such as those described in U.S. Pat. Nos. 4,536,479; 4,233,401; 4,233,402 and 3,996,345, whose disclosures are incorporated herein by reference, can be used.

In preferred embodiments, the first immunoreactant of step (d) is further prepared for assaying according to step (e) by the following steps:

(i) Admixing a biologically active labeled specific binding agent, preferably a receptor, that binds to any human immunoglobulin present in the first immunoreactant to form a complex, preferably a labeled second immunoreactant. More preferably, the labeled second immunoreactant. More preferably, the labeled specific binding agent is immunoglobulin class-specific; i.e., the binding agent is capable of immunoreacting specifically with an immunoglobulin of the IgG, IgM or IgA classes, as is illustrated hereinafter. The labeled specific binding agent is capable of signaling the presence of the specific binding agent in a complex.

(ii) The labeled specific binding agent/first immunoreactant admixture so formed is maintained under biological assay conditions for a predetermined time period sufficient for the labeled specific binding agent to form a complex with any anti-EA-D antibodies present as first immunoreactant.

Assaying for the presence of the labeled specific binding agent bound as part of the second immunoreactant that contains anti-EA-D antibody provides an assay for the presence of anti-EA-D antibodies in the sample. In preferred embodiments, the amount of the labeled second specific binding agent bound as part of the complex is determined, and thereby the amount of anti-EA-D antibodies in the sample. That amount can be zero, thereby indicating no anti-EA-D antibodies are present in the sample, within the limits that can be detected. Methods for assaying for the presence and amount of a labeled specific binding agent depend on the label used, such labels and assay methods being well known in the art.

The labeling of proteinaceous specific binding agents such as receptors in the form of whole antibodies is well known in the art. For instance, receptors produced by hybridomas can be labeled by metabolic incorporation of radioisotope-containing amino acids provided as a component in the tissue culture medium. See for example Galfre et al., *Meth. Enzymol.* 73, 3–46 (1981). The techniques of protein conjugation or coupling through activated functional groups are particularly applicable. See, for example, Aurameas et al., *Scand. J. Immunol. Vol.* 8, *Suppl.* 7, 7–23 (1978) and U.S. Pat. No. 4,493,795, whose disclosures are incorporated herein by reference.

In addition, a site-directed coupling reaction can be carried out so that the label does not substantially interfere with the immunoreaction of the second receptor with its target antigen. See, for example, Rodwell et al., *Biotech.* 3, 889–894 (1985).

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As A Tool*, Marchalonis, et al., eds., John Wiley & Sons, Ltd., pp. 189231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azinodi-(3-ethylbenzthiazoline-G-sulfonic acid) (ABTS). Radioactive elements are also useful labeling agents and are used illustratively herein.

An exemplary radiolabeling agent is a radioactive element that produces gamma ray emissions. Elements which themselves emit gamma rays, such as $^{124}I$, $^{125}I$, $^{128}I$, $^{131}I$, $^{132}I$ and $^{51}Cr$ represent one class of gamma ray emissionproducing radioactive element indicating groups. Particularly preferred is $^{125}I$. Another group of useful labeling means are those elements such as $^{11}C$, $^{18}F$, $^{15}O$ and $^{13}N$ themselves emit positrons. The positrons so emitted produce gamma rays upon encounters with electrons present in the animal's body. Also useful is a beta emitter, such as $^{111}$indium or 3H.

The assay methods and systems of the present invention can utilize an antigen or receptor of this invention affixed to solid matrix to form a solid support.

The antigen or receptor is typically affixed to the solid matrix by adsorption from an aqueous medium although several modes of adsorption, as well as other modes of affixation well known to those skilled in the art can be used. Exemplary of such modes are the reaction of the receptor or antigen with the reactive carboxyl functionality produced by the reaction of cyanogen bromide with glucosecontaining matrices such as cross-linked dextrose or cellulose, glutaraldehyde linking as discussed hereinafter in conjunction with latex particles and the like.

Useful solid matrices are well known in the art. Such materials include the cross-linked dextran available under the trademark SEPHADEX from Pharmacia Fine Chemicals (Piscataway, NJ); agarose; beads of polystyrene beads about 1 micron to about 5 millimeters in diameter available from Abbott Laboratories of North Chicago, IL; polyvinyl chloride, polystyrene, cross-linked polyacrylamide, nitrocellulose of nylon-based webs such as sheets, strips or paddles; glass; or tubes, plates or the wells of a microtiter plate such as those made from polystyrene or polyvinylchloride.

Latex particles useful in agglutination-type assays are also useful solid matrices. Such materials are supplied by the Japan Synthetic Rubber Company of Tokyo, Japan, and are described as carboxy-functional particles dispersed in an anionic soap. Typical lots of such particles dispersed in an anionic soap. Typical lots of such particles dispersed in an average diameter of 0.308 microns, and have an average carboxyfunctional group distribution of about 15 to about 30 square Angstroms per carboxy group.

Prior to use, the particles are reacted with a diamine such as 1,3-diamino-3-propanol to form a plurality of amide bonds with the particle carboxy groups while maintaining free amino groups. The free amines are thereafter reacted with dialdehyde such as glutaraldehyde and the receptor or antigen to form Schiff base reaction products. The Schiff base reaction products are thereafter reduced with a water-soluble reductant such as sodium borohydride to provide a useful solid support.

Those skilled in the art will understand that there are numerous immunoassay methods that can be utilized herein. However, any method that results in a signal imparted by the reaction of anti-EA-D antibody with a polypeptide of this invention is contemplated. Further, while the particularly described assay systems and methods utilize a solid phase, the invention is not so limited. Each of those assay methods can employ single or double antibody techniques in which an indicating means is utilized to signal the immunoreaction, and thereby the binding of antibody that is to be assayed with a polypeptide of this invention. Exemplary techniques can be found explained in Maggio, *Enzyme Immunoassay*, CRC Press, Cleveland, OH (1981); and in Goldman, *Fluorescent Antibody Methods*, Academic Press, New York, NY (1980).

2. Diagnostic System for Assaying Anti-EA-D Antibodies

A diagnostic system, preferably in kit form, useful for carrying out the anti-EA-D antibody assay methods of this invention includes, in separate packages, (a) a synthetic polypeptide consisting essentially of about 6 to about 40 amino acid residues having an amino acid residue sequence substantially corresponding to an amino acid residue sequence of the EBV EA-D protein from about position 350 to about position 362 from the amino terminus thereof, said polypeptide having the capacity to be immunologically bound by antibodies induced by EA-D, and (b) a labeled specific binding agent for signaling the immunoreaction of anti-EA-D antibodies with the polypeptide. Preferably, the labeled specific binding agent is a receptor linked to an enzyme.

In preferred embodiments, the system further includes a solid matrix to which the polypeptide can be affixed to form a solid support. Useful solid matrices have already been described. Preferably, however, the solid matrix is the well of a microtiter plate. Most preferably the solid support is provided with a known amount of polypeptide affixed to the solid matrix.

In preferred embodiments the system also includes antibodies raised to a polypeptide of the invention for use as a positive control.

Known amounts of the polypeptide and labeled specific binding agent are provided. Those amounts are at least enough to carry out one assay. The polypeptide and labeled specific binding agent are typically provided in a form and amount that is designed to be diluted to a proscribed volume with water, saline or a buffer such as described hereinbelow.

Additional packages can also be included in the system. Such packages can contain (i) buffer salts in dry or liquid form, (ii) enzyme substrates such as o-phenylenediamine, and the like.

3. Assays for EA-D

A method for assaying for the presence of EA-D in a body sample is also contemplated herein. In general, a body sample to be assayed is provided, such as lysed peripheral blood lymphocytes (PBL) lysed by acetone or methanol fixation. The sample is admixed with receptor molecules that contain an antibody combining site induced by a synthetic polypeptide of this invention. The admixture is maintained under biologically assay conditions for a predetermined period of time sufficient for the receptor molecules to immunoreact with EA-D present in the body sample. The amount of that immunoreaction (i.e., the amount of immunoreactant formed) is then measured to determine whether EA-D molecules were present or absent in the assayed body sample.

4. Diagnostic System for Assaying EA-D

A diagnostic system, preferably in kit form, useful for carrying out the above assay method includes, in separate packages, (a) receptors of this invention that immunoreact with EA-D, (b) a labeled specific binding agent for signaling the immunoreaction of the receptors of this invention with EA-D.

In preferred embodiments, the kit further includes, in a separate package, an amplifying reagent such as complement, like guinea pig complement, anti-immunoglobulin antibodies or S. aureus cowan strain protein A that reacts with the receptors. In these embodiments, the labeled specific binding agent is capable of specifically binding the amplifying means when the amplifying means is bound to a receptor of this invention.

Receptor molecules and separate indicating means of any diagnostic system described herein, as well as the above described amplifying reagent, can be provided in solution, as a liquid dispersion or as a substantially dry power, e.g., in lyophilized form. Where the indicating means is a separate molecule from the amplifying reagent, it is preferred that the indicating means be packaged separately. Where the indicating means is an enzyme, the enzyme's substrate can also be provided in a separate package of the system. A solid matrix such as the before-described microscope slide, one or more buffers and acetone can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

BEST MODE FOR CARRYING OUT THE INVENTION

The following examples are intended to illustrate, but not limit, the present invention.

EXAMPLE 1 :

Synthesis of Polypeptides

To locate the EA-D gene and determine its reading frame, a portion of the amino-terminus of the EA-D protein was sequenced using affinity purified EA-D. The amino acid residue sequence thus obtained was compared to possible amino acid residue sequence translations of the EBV genome until a match was found, thereby identifying the putative EA-D gene and its reading frame. Based upon that reading frame the translated amino acid residue sequence of the EA-D protein gene is shown in FIG. 1 for the EBV strain utilized by Baer et al., *Nature* 310, 207 (1984).

Using the above-obtained amino acid residue sequence, a series of short synthetic polypeptides corresponding to portions of that translated gene were synthesized and examined for their ability to mimic antigenic determinants of native EA-D. The amino acid residue sequences of those polypeptides and the locations of their sequences in the EA-D protein from the amino-terminus are shown, from left to right and in the direction of amino-terminus to carboxy-terminus, in Table 1 below.

TABLE 1

| Synthetic Polypeptides Derived from EA-D Molecule | | |
|---|---|---|
| Designation | Sequence | Location[1] |
| K7 | PARPETPSPAIPSC[2] | 350–362 |
| K6 | RKRTSSEARQKQKC[2] | 379–391 |
| K5 | PKKVKQAFNPLIC[2] | 393–404 |
| K8 | TVSPSPSPPPPPRTPC[2] | 331–345 |
| K9 | SVAADSLAAALSLC | 242–255 |

[1]Location from the amino-terminus of the EA-D molecule as translated and predicted from the genomic sequence data reported in Baer et al., Nature, 310, 207 (1984).
[2]Carboxy-terminal cysteine added for purposes of coupling is not present in the cognate EA-D protein amino acid residue sequence.

The polypeptides shown in Table 1, above, were chemically synthesized by solid-phase methods as described in Merrifield et al., *J. Am. Chem. Soc.*, 85, 2149–2154 (1963) and Houghten, et al., *Int. J. Pept. Prot. Res.* 16, 311–320 (1980). The solid phase method of polypeptide synthesis was practiced utilizing a Vega Model 250C Polypeptide Synthesizer, available commercially from Vega Biotechnologies, Inc., Tucson, AZ.

For polypeptides other than K9 a cysteine residue was added to the carboxyl-terminus to assist in coupling to a protein carrier as described below. The composition of all polypeptides were confirmed by amino acid analysis.

In preparing a synthetic polypeptide of this invention by the above solid phase method, the amino acid residues were linked to a resin (solid phase) through an ester linkage from the carboxy-terminal residue. If the polypeptide is to be linked to a carrier via a Cys residue or polymerized via terminal Cys residues, it is convenient to utilize that Cys residue as the carboxy-terminal residue that is ester-bonded to the resin.

The alpha-amino group of each added amino acid was typically protected by a tertiarybutoxycarbonyl (t-BOC) group prior to the amino acid being added into the growing polypeptide chain. The t-BOC group was then removed prior to addition of the next amino acid to the growing polypeptide chain.

Reactive amino acid side chains were also protected during synthesis of the polypeptides. Usual side-chain protecting groups were used for the remaining amino acid residues as follows: 0-(p-bromobenzyloxycarbonyl) for tyrosine; 0-benzyl for threonine, serine, aspartic acid and glutamic acid; S-methoxybenzyl for cysteine, dinitrophenyl for histidine; 2-chlorobenzoxycarbonyl for lysine and tosyl for arginine.

Prior to use, protected amino acids were recrystallized from appropriate solvents to give single spots by thin layer chromatography. Couplings were typically carried out using a ten-fold molar excess of both protected amino acid and dicyclohexyl carbondiimide over the number of milliequivalents of initial N-terminal amino acid. A two molar excess of both reagents can also be used. For asparagine, an equal molar amount of N-hydroxy-benzotriazole was added to the protected amino acid and dimethyl formamide was used as the solvent. All coupling reactions were more than 99% complete by the picric acid test of Gisin, *Anal. Chem. Acta.* 58, 248-249 (1972).

After preparation of a desired polypeptide, a portion of the resulting, protected polypeptide (about 1 gram) was treated with two milliliters of anisole, and anhydrous hydrogen fluoride, about 20 milliliters, was condensed into the reaction vessel at dry ice temperature. The resulting mixture was stirred at about 4 degrees C. for about one hour to cleave the protecting groups and to remove the polypeptide from the resin. After evaporating the hydrogen fluoride at a temperature of 4 degrees C. with a stream of $N_2$, the residue was extracted with anhydrous diethyl ether three times to remove the anisole, and the residue was dried in vacuo.

The vacuum dried material was extracted with 5% aqueous acetic acid (3 times 50 milliliters) to separate the free polypeptide from the resin. The extract-containing solution was lyophilized to provide a monomeric unoxidized polypeptide.

EXAMPLE 2:

Preparation of Oligomers

A synthetic oligomer of this invention can be prepared by the solid phase synthesis of a plurality of the polypeptides of this invention linked together end-to-end (head-to-tail) by an amide bond between the carboxyl-terminal residue of one polypeptide and the amino-terminal residue of a second polypeptide. Such synthetic oligomers are preferably synthesized as a single long polypeptide oligomer, but can also be prepared as individual polypeptides that are linked together subsequent to their individual syntheses, using a carbodiimide reagent such as 1-(3dimethylaminoproply)-3-ethylcarbodiimide hydrochloride in water. The total number of amino acid residues contained in an oligomer prepared as a single polypeptide chain is preferably less than about 40, so that up to about six polypeptides of this invention can be incorporated into a single head-to-tail oligomer chain that is synthesized as a single polypeptide. A synthetic head-to-tail oligomer more preferably contains two to about four blocks of linked, synthetic polypeptides of this invention, and a total of less than about 40 amino acid residues.

EXAMPLE 3:

Preparation of Polymers

A polypeptide polymer (synthetic multimer) of this invention can be prepared by synthesizing a polypeptide of this invention, as discussed in Example 1, and including cysteine residue at both the amino- and carboxy-termini to form a "diCysterminated" polypeptide is un-oxidized, reduced form. After synthesis, in a typical laboratory preparation, 10 milligrams of the diCys polypeptide (containing cysteine residues in unoxidized form) are dissolved in 250 milliliters (ml) of 0.1 molar (M) ammonium bicarbonate buffer. The dissolved diCysterminated polypeptide is then air oxidized by stirring the resulting solution gently for a period of about 18 hours in the air at ambient norm temperature, or until there is no detectable free mercaptan by the Ellman test. [Ellman, *Arch. Biochem. Biophys.*, 82, 70-77 (1959).]

The polymer so prepared contains a plurality of the synthetic polypeptide repeating units that are bonded together by oxidized cysteine (cystine) residues. Such polymers typically contain their polypeptide repeating units bonded together in a head-to-tail manner as well as in head-to-head and tail-to-tail manners; i.e., the amino-termini of two polypeptide repeating units can be bonded together through a single cystine residue as can two carboxyl-termini since the linking groups at both polypeptide termini are identical.

EXAMPLE 4:

Coupling to Carriers

The synthetic polypeptides were coupled to keyhole limpet hemocyanin (KLH) as immunogenic carrier by the method described in Liu et al., *Biochem.*, 80, 690 (1979). Briefly, 4 milligrams (mg) of the carrier were activated with 0.51 mg of m-maleimidobenzoyl-N-hydroxysuccinimide ester, and were subsequently reacted with 5 mg of the polypeptide through an amino- or carboxy-terminal cysteine to provide a conjugate containing about 10 to about 35% by weight polypeptide.

EXAMPLE 5:

ELISA Assay for Anti-EA-D Antibody

Serum samples from patients with a variety of EBV-associated clinical conditions were assayed for the presence of anti-EA-D antibodies using the ELISA described below. The sera assayed were from patients diagnosed as having acute infectious mononucleosis (IM), based on their clinical features and a positive sheep red blood cell agglutination (i.e., heterophile). To confirm the IM diagnosis, convalescent sera from these patients were examined for and found to contain anti-EBNA-1 and anti-VCA (VCA') antibodies.

Normal adult sera were obtained from healthy individuals who were negative for antibodies directed against heterophile, VCA and EBNA-1 antigens. This group, designated VCA negative (VCA—) presumably had not undergone primary EBV infection. A second group of healthy normal donors had positive anti-VCA and anti-EBNA-1 antibody titers. This second control group, designated VCA positive (VCA+), had presumably undergone prior exposure to EBV.

Sera from patients with acute cytomegalovirus (CMV) infection, as determined by increased convalescent anti-CMV antibody titers, were also examined. The sera examined from patients with Sjogren's Syndrome (SS) had keratoconjunctivitis sicca, xerostomia, positive minor salivary gland biopsy (grade IV on a scale from I to IV), and elevated autoantibody titers including anti-nuclear antigen and rheumatoid factor. Also evaluated were sera from patients with rheumatoid arthritis (RA) but lacking associated SS symptoms.

Synthetic polypeptide was affixed to the walls of microtiter plate wells (Immunolon II; Dynatech Laboratories, Inc., Alexandria, VA) as matrix by admixing to each well 0.050 ml of borate-buffered saline (BBS; 200 mM sodium borate, 160 mM NaCl, pH 8.0) containing 10 micrograms per milliliter (ug/ml) polypeptide. The admixture was maintained for about 16 hours at about 4 degrees C. Non-bound polypeptide was separated from the wells by inverting the plates and shaking. Residual non-specific binding sites were then blocked by admixing 0.200 ml of blocking solution [PBS (10 mM sodium phosphate, 150 mM NaCl, pH 7.3) containing 10% normal goat serum (NGS)] into each well. The admixtures so formed were maintained for about 90 minutes at 37 degrees C. in a humidified chamber. The blocking solution was then removed from the wells by inverting and shaking, and solid supports so formed allowed to dry in air for about one hour at 37 degrees C.

To each of the polypeptide-coated wells (solid supports) were admixed 0.200 ml of serum diluted 1:20 in blocking solution to form a solid-liquid phase immunoreaction admixture. The admixtures were maintained for about 1 hour at 25 degrees C. Non-bound material was then separated from the wells by washing 3 times with BBS containing 0.05% Tween 20 [polyoxyethylene (30) sorbitan monolaurate] (Sigma).

The amount of solid phase-affixed immunoreactant formed was determined by admixing 0.200 ml of a human immunoglobulin class specific antibody linked to horse radish peroxidase (HRP) diluted 1:1000 in BBS containing 10% NGS to form a second solid liquid phase admixture. To detect IgG and IgM antibodies, HRP-linked mouse anti-human IgG and mouse anti-human IgM monoclonal antibodies were used, respectively (Ortho Diagnostics, Raritan, NJ). To detect IgA antibodies, HRP-linked goat anti-human IgA was used (Kiregaard and Perry, Gaithersburg, MD). The second solid/liquid phase admixtures were maintained for about one hour at about 25 degrees C. Non-bound material was then separated from the solid phase-affixed sandwich (second) immunoreactant by washing 5 times as described above.

The amount of solid phase affixed sandwich (second) immunoreactant-containing HRP label was then assayed by admixing 0.200 ml of o-phenylenediamine (OPD, Sigma) substrate solution freshly prepared according to the supplier's instructions. Color was allowed to develop for a time period of about 15 to about 30 minutes of about 25 degrees C. The substrate conversion reaction was then stopped by admixing into each well 0.050 ml of 4N $H_2SO_4$. The optical density (O.D.) of the admixtures was determined at a 490 nanometer (nm) wavelength using a Dynatech MR6000 (Dynatech Laboratories, Inc.) microtiter plate reader.

Figure 2:
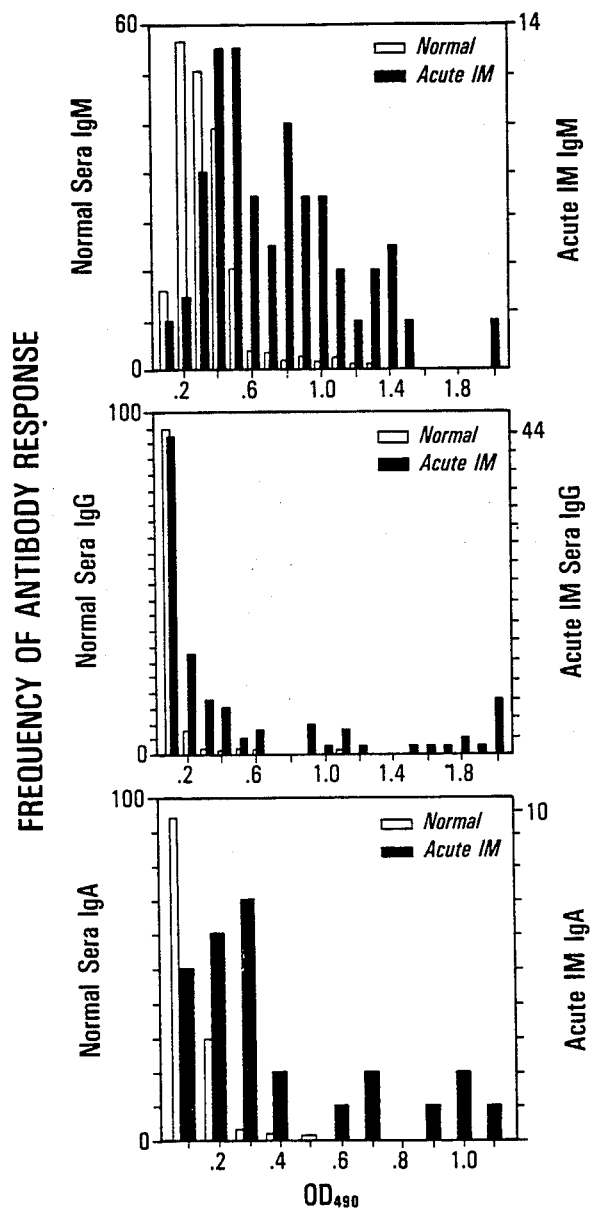
FIG. 2 contains three graphs that illustrate the results of assaying for anti-EA-D IgM, IgG and IgA antibodies, respectively, in sera from normal individuals (Normal) and infectious mononucleosis patients (Acute IM) using the anti-EA-D antibody ELISA with polypeptide K7 as solid phase target as described in Example 5. Serum samples were obtained from 44 patients with acute IM (solid bars) and from 194 healthy normal individuals (open bars) including 40 with no prior exposure to EBV (VCA−). The optical density at 490 nanometers (nm) (OD 490) produced by each sample in the assay was rounded to the nearest one-tenth unit, and is the abscissa of each graph. Each bar represents the number of samples that produced the indicated OD 490.

The results of assaying the IM and normal sera for anti-EA-D antibodies are shown in FIG. 2. Using polypeptide K7 bound to the solid matrix, significantly higher binding of IgG, IgA and IgM antibodies from IM patients' sera as compared to normal sera was observed. In contrast, synthetic polypeptides K5, K8 and K9 did not exhibit increased immunoreactivity with IM sera as compared to the normal sera. However, a low immunoreactivity against polypeptide K6 was present in some IM sera.

Sera from patients with naso-pharyngeal carcinoma (NPC), an EBV-related disease, and with SS also exhibited increased immunoreactivity with polypeptide K7 in comparison to normal sera (FIG. 3). In contrast, sera from patients with RA lacking sicca symptoms did not show significant antipolypeptide K7 activity.

A time course study was also performed using the above described ELISA. Serial samples from four IM patients obtained during a period when they suffered IM symptoms were examined for the presence of anti-K7 and anti-EBNA-1 antibodies, using polypeptide K7 and polypeptide of Rhodes et al., *J. Immunol.*, 134, 211-16 (1985), respectively affixed to the solid matrix. Those results, shown in FIG. 4, indicate that anti-EA-D polypeptide antibodies occur at higher levels at the onset of EBV infection than do anti-EBVA-1 antibodies.

Thus, the assay method of this invention can detect antibodies that immunologically lind to a polypeptide of this invention in the sera patients with EBV-associated disease. It is believed that these polypeptide-reactive antibodies were induced by corresponding portions of the EA-D protein as a result of EBV infection.

EXAMPLE 6:

Polypeptide Concentration

The effects of varying the concentration of the polypeptide containing solution used to coat the walls of microtiter plate wells to form solid supports was examined. Solutions containing 0.1, 1.0, 10 and 100 ug/ml of polypeptide K7 in BBS were used to affix polypeptide to the well walls as described in Example 5. An ELISA to detect anti-EA-D IgM antibodies was performed according to Example 5 using sera from normal individuals (VCA+ and VCA−) and from an IM patient. All sera were used at a 1:20 dilution.

The results of this study are shown in FIG. 5A. Those results indicate that the amount of anti-EA-D IgM antibody detected in each of the assayed sera did not vary substantially over the range of polypeptide concentrations examined. Thus, a polypeptide solution with a concentration as low as 0.1 ug/ml polypeptide can be used to affix a polypeptide of this invention to the inner walls of a microtiter plate well to form a solid support.

EXAMPLE 7:

Sample Dilution

The effects of diluting the body fluid sample to be assayed in the ELISA of Example 5 were also examined. Sera from normal individuals (VCA− and VCA+) and from patients with IM, NPC or SS were diluted 1:5, 1:20, 1:50 and 1:100 in the before discussed blocking solution, and were assayed as described in Example 5.

The results of this study are shown in FIG. 5B. Those results indicate that the decrease in sensitivity associated with increasing dilution of sample begins to level off at a sample dilution of about 1:20.

EXAMPLE 8:

Detection of Anti-EA-D Immunoglobulin Class

The ability of the assay methods of the present invention to differentiate the classes of anti-EA-D immunoglobulin present in a sample was examined. This was accomplished using each of the polypeptides shown in Table 1 as a solid phase-affixed antigen in the ELISA of Example 5.

The results of assaying the polypeptides in Table 1 for their abilities to immunoreact with IgG, IgM and IgA antibodies in serum samples are shown in Table 2 below.

TABLE 2

Binding of IgG, IgM and IgA Antibodies to Various Polypeptides+

| Sample | PEPTIDE[2] | | | | |
|---|---|---|---|---|---|
| | K5 | K6 | K7 | K8 | K9 |
| *IgG* | | | | | |
| R.S.[3] | 0.006 | 0.002 | 0.002 | 0.000 | 0.000 |
| 2241[4] | 0.002 | 0.024 | 0.207 | 0.025 | 0.012 |
| A.W.[5] | 0.000 | 0.000 | 0.000 | 0.000 | 0.003 |
| R.R.[5] | 0.000 | 0.005 | 0.008 | 0.003 | 0.020 |
| D.M.[6] | 0.000 | 0.016 | 0.004 | 0.000 | 0.008 |
| *IgM* | | | | | |
| R.S. | 0.060 | 0.057 | 0.052 | 0.041 | 0.042 |
| 2241 | 0.357 | 0.298 | 0.540 | 0.558 | 0.314 |
| A.W. | 0.107 | 0.167 | 0.101 | 0.100 | 0.080 |
| R.R. | 0.144 | 0.083 | 0.070 | 0.081 | 0.047 |
| D.M. | 0.405 | 0.566 | 0.330 | 0.308 | 0.295 |
| *IgA* | | | | | |
| R.S. | 0.002 | 0.009 | 0.000 | 0.000 | 0.007 |
| 2241 | 0.015 | 0.018 | 0.296 | 0.021 | 0.021 |
| A.W. | 0.000 | 0.051 | 0.000 | 0.003 | 0.006 |
| R.R. | 0.018 | 0.034 | 0.000 | 0.002 | 0.025 |
| D.M. | 0.007 | 0.020 | 0.000 | 0.000 | 0.003 |

[1]Values shown are in units of optical density relative to BBS at a light wavelength of 490 nanometers.
[2]Polypeptides K5, K6, K7, K8 and K9 have the amino acid residue sequences shown in TABLE 1.
[3]Serum from a clinically normal individual with no previous exposure to EBV (VCA−).
[4]Serum from a patient with a clinically acute EBV infection (IM).
[5]Serum from a clinically normal individual previously exposed by EBV (VCA+).
[6]Serum from a clinically normal individual previously exposed to EBV (VCA+) but having an elevated antiEA IgM level (false positive).

The above results indicate that polypeptide K7 affixed (as by adsorption) to a solid matrix to form a solid support has the ability to immunoreact with IgG, IgM and IgA antibodies in the serum of a patient (#2241) having an acute EBV infection. Furthermore, sera from 2 clinically normal individuals containing antibodies to EBV capsid antigen (VCA+) *did not immunoreact with K7*, nor did the serum from a clinically normal individual with no previous detectable exposure to EBV (VCA−).

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A synthetic polypeptide consisting essentially of 13 to about 40 amino acid residues having an amino acid residue sequence corresponding to an amino acid residue sequence represented by the formula:

—PARPETPSPAIPS—, said synthetic polypeptide having the capacity to immunologically bind antibodies raised to EA-D.

2. A synthetic polypeptide wherein the amino acid residue sequence of the polypeptide corresponds to the sequence, taken from left to right and in the direction from amino-terminus to carboxy terminus, represented by the formula:

*PARPETPSPAIPS.*

3. A synthetic polypeptide oligomer containing a total of 13 to about 40 amino acid residues and including a plurality of joined synthetic polypeptide repeating that consist essentially of a polypeptide of claim 1, said oligomer having the capacity to bond antibodies induced by EA-D.

4. A synthetic polypeptide polymer containing a plurality of synthetic polypeptide repeating units joined together by other than polypeptide bonds and containing more than about 100 amino acid residues, said units consisting essentially of 13 to about 40 amino acid residues having a sequence corresponding to an amino acid residue sequence represented by the formula:

—PARPETPSPAIPS—, said polymer being water-dispersible at a pH value of about 5 to about 9 and having the ability to immunoreact with antibodies induced by EA-D.

5. A method for assaying a body fluid sample for the presence of antibodies to EA-D comprising the steps of:
   (a) providing a body fluid sample to be assayed;
   (b) providing a synthetic polypeptide containing 13 to about 40 amino acid residues having an amino acid residue sequence corresponding to an amino acid residue sequence represented by the formula:

—PARPETPSPAIPS—, said synthetic polypeptide having the capacity to immunologically bind antibodies induced by EA-D;
   (c) admixing the body fluid sample with the polypeptide to form a first immunoreaction admixture;
   (d) maintaining the admixture under biological assay conditions for a predetermined time period sufficient for any anti-EA-D antibodies present in the sample to immunologically bind to the polypeptide to form a first immunoreactant; and
   (e) determining the presence of any first immunoreactant formed in said admixture and thereby the presence of said antibodies in said sample.

6. The method of claim 5 wherein said body fluid sample is either serum or plasma.

7. The method of claim 6 wherein the first immunoreactant is labeled prior to determining according to step (e) by:
   (a) admixing a biologically active labeled receptor that binds to human immunoglobulin present in the first immunoreactant to form a labeled second immunoreactant, said labeled receptor being capable of signalling the presence of said labeled receptor in said second immunoreactant; and
   (b) maintaining the admixture so formed under biological assay condition for a predetermined period of time sufficient for said labeled receptor to form a second immunoreactant with any anti-EA-D antibodies present as first immunoreactant; and
   (c) determining the presence of the labeled immunoreactant.

8. The method of claim 7 wherein said polypeptide is affixed to a solid matrix as a solid support.

9. A diagnostic kit for assaying for the presence of anti-EA-D antibodies in a body fluid sample comprising in separate packages:
 (a) a synthetic polypeptide consisting essentially of 13 to about 40 amino acid residues having an amino acid residue sequence substantially corresponding to an amino acid residue sequence represented by the formula:

—PARPETPSPAIPS—, said polypeptide having the capacity to be immunologically bound by antibodies induced by EA-D; and
 (b) a labeled specific binding agent for signaling the immunoreaction of anti-EA-D antibodies with the polypeptide.

10. The diagnostic system of claim 9 wherein said polypeptide is affixed to a solid matrix.

11. The diagnostic system of claim 9 wherein said labeled specific binding agent is an enzyme-labeled receptor.

12. The diagnostic system of Claim 11 wherein said labeled receptor is human immunoglobulin class-specific.

13. An inoculum comprising an effective amount of a synthetic polypeptide consisting essentially of 13 to about 40 amino acid residues having a sequence corresponding to an amino acid residue sequence represented by the formula:

—PARPETPSPAIPS—, said polypeptide linked to a carrier and dispersed in a physiologically tolerable diluent.

14. A receptor raised to a synthetic polypeptide, said polypeptide consisting essentially of 13 to about 40 amino acid residues having a sequence corresponding to an amino acid residue sequence represented by the formula:

—PARPETPSPAIPS—, said receptor being capable of immunoreacting with the EA-D protein.

15. A method of assaying for the presence of EA-D in a body sample consisting essentially of lysed peripheral blood lymphocytes comprising the steps of:
 (a) admixing the sample with receptors to form an immunoreaction admixture, said receptors raised to a synthetic polypeptide consisting essentially of 13 to about 40 amino acid residues having a sequence corresponding to an amino acid residue sequence represented by the formula:

—PARPETPSPAIPS—;

(b) maintaining the admixture under biological assay conditions for a predetermined time period sufficient for any EA-D present in the sample to immunoreact with the receptors to form an immunoreactant; and
 (c) determining the presence of any immunoreactant formed in said admixture and thereby the presence of said antibodies in said sample.

16. A diagnostic kit for assaying for the presence of EA-D in a body sample comprising in separate packages:
 (a) receptors raised to a synthetic polypeptide consisting essentially of 13 to about 40 amino acid residues having a sequence corresponding to an amino acid residue sequence represented by the formula:

—PARPETPSPAIPS—, said receptors being capable of immunoreacting with the EA-D protein; and
 (b) a labeled specific binding agent for signaling the immunoreaction of the receptors with EA-D protein.

17. A method for assaying a human body fluid sample for the amount of IgA, IgM or IgG antibodies to EA-D comprising the steps of:
 (a) providing a serum or plasma sample to be assayed;
 (b) admixing the body fluid sample with the solid support to form a first immunoreaction admixture, said solid support comprising a solid matrix having affixed thereto a synthetic polypeptide having an amino acid residue sequence, taken from left to right and in the direction from amino-terminus to carboxy-terminus, represented by the formula:

PARPETPSPAIPS;

(c) maintaining under biological assay conditions for a predetermined time period sufficient for any anti-EA-D antibodies present in the sample to immunologically bind to the polypeptide of the solid support to form a first immunoreactant;
 (d) thereafter separating said solid support from said body fluid sample;
 (e) admixing said separated solid support with biologically active labeled receptors to form a second immunoreaction admixture, said labeled receptors being immunoglobulin class-specific and capable of binding to and signaling the presence of any human immunoglobulin of classes IgA, IgM or IgG, respectively, present as first immunoreactant;
 (f) maintaining the second immunoreaction mixture so formed under the biological assay conditions for a predetermined period of time sufficient for said labeled receptors to form a second immunoreactant with any IgA, IgM or IgG antibodies to EA-D present as first immunoreactant;
 (g) separating the solid support from any labeled receptors not bound as second immunoreactant; and
 (h) determining the amount of labeled receptors present as second immunoreactant and thereby the amount of IgA, IgM or IgG antibodies present in said body fluid sample.

* * * * *